US00PP34285P2

(12) United States Plant Patent
Hansen

(10) Patent No.: US PP34,285 P2
(45) Date of Patent: May 31, 2022

(54) ***HOSTA* PLANT NAMED 'WHEN I DREAM'**

(50) Latin Name: *Hosta hybrid (Trait.)*
Varietal Denomination: When I Dream

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/300,992

(22) Filed: Jan. 10, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02; A01H 5/12
See application file for complete search history.

*Primary Examiner* — Kent L Bell

(57) ABSTRACT

A new and distinct *Hosta* plant named 'When I Dream' producing large-sized rounded mounds of basal, cordate, leaves with acute apices, cordate bases and slightly wavy margins. The leaves are variegated having deep green margins and centers that begin the season chartreuse and become lutescent as the season progresses with intermediate color separation between the margin and center of variably large segments of several shades of chartreuse. The campanulate flowers are near white with light lavender just above the foliage beginning in mid-June. 'When I Dream' is useful in the landscape, as a container plant, a specimen or en masse.

2 Drawing Sheets

Botanical classification: *Hosta* hybrid (Trait.).
Variety denomination: 'When I Dream'.

STATEMENT REGARDING PRIOR DISCLOSURES UNDER 37 CFR 1.77(B)(6)

*Hosta* 'When I Dream' was first introduced by the inventor as a non-enabling description in registration of the name in early 2021 with the International Cultivar Registration Authority for the genus *Hosta*. No plants of *Hosta* 'When I Dream' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'When I Dream' hereinafter also referred to as the new plant or by the cultivar name, 'When I Dream'. *Hosta* 'When I Dream' was hybridized by the inventor on Jul. 1, 2011 at a wholesale perennial nursery in Zeeland, Mich., USA. The female parent was the proprietary unreleased streaked sport of 'Empress Wu' (not patented) and the male parent was 'Queen of the Seas' (not patented). The female sport parent, 'Empress Wu' is U.S. Plant Pat. No. 20,774. The seeds from this cross were collected and planted on Nov. 7, 2011 and a single seedling selection from this cross eventually produced the new plant. The new plant was assigned the breeder code 11-449-2 and passed the initial evaluation in the summer of 2018. 'When I Dream' has been asexually propagated by division at the same nursery since 2018 and also by careful shoot tip plant tissue culture with the resultant asexually propagated plants having retained all the same traits as the original plant. *Hosta* 'When I Dream' has been stable and reproduced true to type plants in successive generations of asexual reproduction.

There are nearly 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Angel Falls' U.S. Plant Pat. No. 28,785, 'American Sweetheart' (not patented), 'Sea Thunder' (not patented), 'Lakeside Paisley Print' (not patented), 'Center of Attention' (not patented), 'Cool As a Cucumber' (not patented), 'Lakeside Love Affair' (not patented), 'Hudson Bay' U.S. Plant Pat. No. 23,598, 'Miss America' U.S. Plant Pat. No. 32,068, 'Jane Ward' (not patented) and 'Viva Las Vegas' (not patented).

The female parent is larger in habit with larger, smoother, and more lustrous leaves of solid green, and the scapes are longer and more arching. 'Queen of the Seas' has a broader and more horizontal habit with more glaucous, solid bluish-green colored foliage.

The habit of 'Angel Falls' is smaller and more arching in habit with leaves more lustrous and more greenish-yellow leaf center earlier in the season, and the margins are more green and less bluish-green. 'American Sweetheart' has more white leaf center and less glaucous surface less significant intermediate variegated colors between the margin and center with the margins being more green and less bluish-green. 'Sea Thunder' has smaller habit and smaller foliage with less intermediate colors between the margin and center, the margins are more green and less bluish-green, and the flowers are more pigmented medium lavender. 'Lakeside Paisley Print' has a more upright habit with margins and narrower center variegation, and the margins are more green and less bluish-green, and the scapes are more cream-colored becoming more lavender blushed, and the flowers are darker purple. 'Center of Attention' has a shorter more rounded leaf without the sinuate margin and bullate surface. 'Cool As a Cucumber' has a longer more lanceolate and arching foliage with less glaucous bullate surface. 'Lakeside Love Affair' has foliage that is more lustrous and broadly ovate with less noticeable intermediate colors between the margin and center variegation. 'Hudson Bay' has a smaller habit and foliage size, the leaves have a more bluish-green margin and white center and lack the sinuate margin and has less noticeable intermediate colors between the center and margin. 'Miss America' has stiffer and thicker foliage with broader margins and narrower variegated leaf center, and the flowers are larger, open wider and have a darker lavender center stripe. 'Jane Ward' has foliage that is more ovate and lustrous, less bullate and glaucous and the flowers are less sinuate and the margin color is more bluish-green. 'Viva Las Vegas' has foliage that is more arching and has narrower margins and wider creamy centers.

Other *Hosta* cultivars may have individual traits similar to 'When I Dream' but the new plant differs from the above listed cultivars and all other *Hostas* known to the applicant, by the combination of the following traits.

1. Leaves are large-sized, cordate, with acute apices and cordate bases;
2. Leaves have a slightly wavy margin, bullate surface between the veins, and slightly impressed adaxial veins;
3. Leaf margins are deep green, the mature center color emerges chartreuse becoming lutescent as the season progresses;
4. Leaves have series of intermediate color separation of several shades of chartreuse between the margin and center of variably large segments;
5. Campanulate flowers are near white on upright, pale green-colored scapes beginning in mid-June;
6. Flowers are densely arranged on scapes with the first flowers beginning to open just above the foliage;
7. The habit is a large-sized rounded mound.

BRIEF DESCRIPTION OF THE DRAWING

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

The drawings show a plant of 'When I Dream' in a trial garden at a nursery in Zeeland, Mich. with supplement fertilizer and water as needed.

DETAILED BOTANICAL DESCRIPTION

Figure 1:
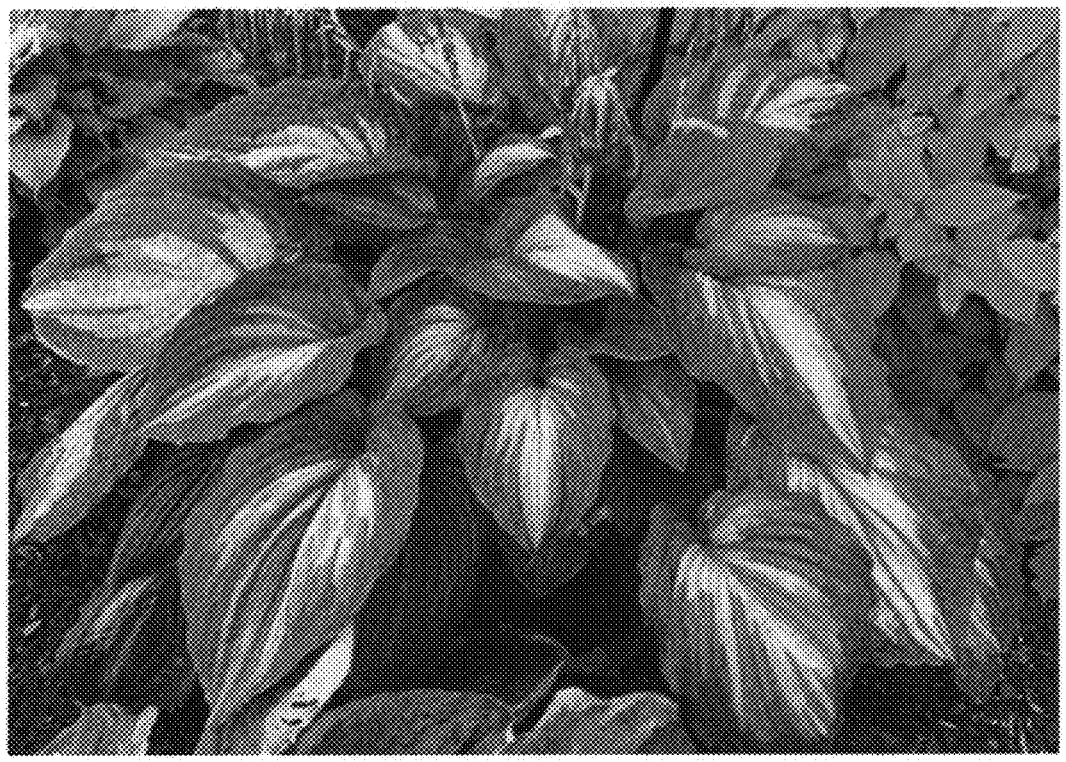
FIG. 1 shows the landscape foliage habit of a nine-year-old plant in late summer.
Figure 2:
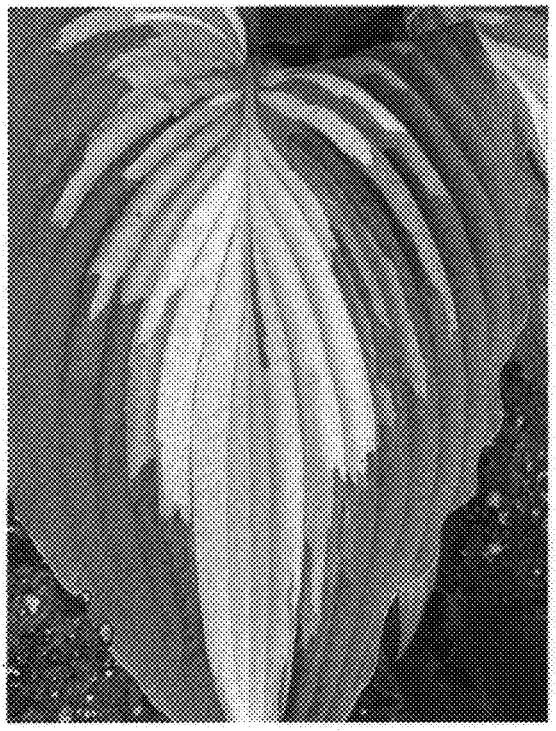
FIG. 2 shows a close-up of a leaf of a nine-year-old plant.
Figure 3:
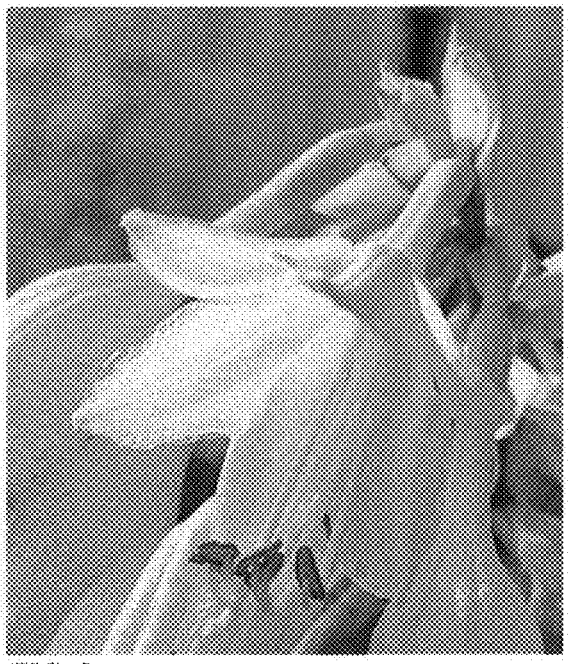
FIG. 3 shows a close-up of the flower, buds and foliar bracts of a nine-year-old plant.
Figure 4:
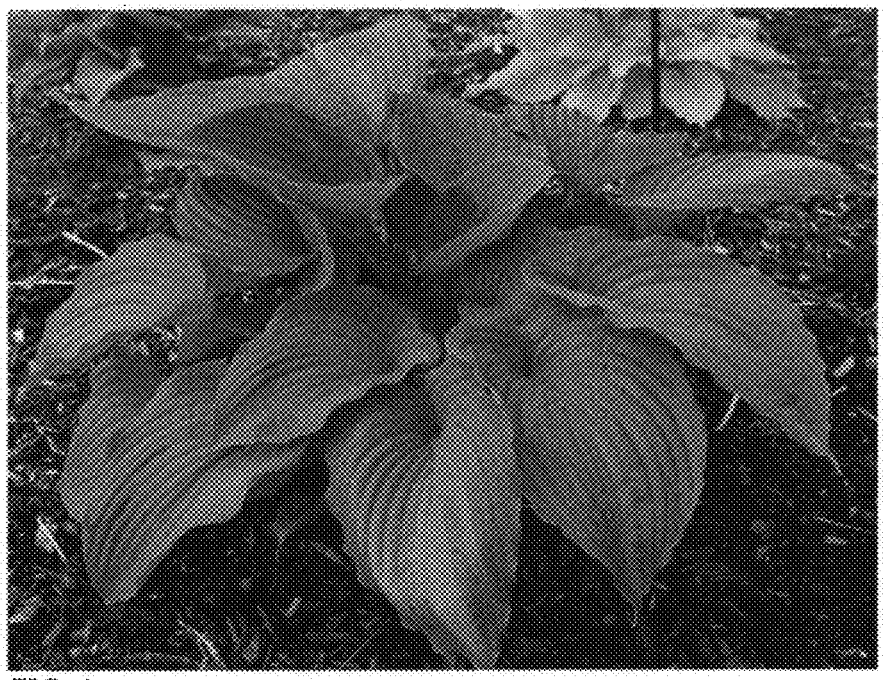
FIG. 4 shows an approximate four-year-old plant with newly emerging foliage with more chartreuse coloration in the center region of the variegated leaves.

The following descriptions and color references are based on the 2015 edition of The Royal Horticultural Society Colour Chart except where common dictionary terms are used. The new plant, *Hosta* 'When I Dream', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a five-year-old plant in a shaded trial garden in Zeeland, Michigan with supplemental water and fertilizer.

Botanical classification: *Hosta* x hybrid;

Parentage: Female or seed parent is a proprietary streaked sport of 'Empress Wu'; male or pollen parent is 'Queen of the Seas';

Propagation: Garden division and sterile shoot tip tissue culture;

Time to initiate roots from tissue culture: About three weeks;

Growth rate: Moderately vigorous to slow;

Crop time: About four months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a large-sized mound of outwardly arching petioles and leaves and mostly erect scapes flowering just above the foliage;

Plant size: Foliage height to about 71.1 cm above soil line to the top of the leaves, to about 86.4 cm tall to the top of the flowers and to about 157.5 cm wide at the widest point just above the soil line;

Foliage description: Cordate; short, narrowly acute apex, cordate base; margin entire, and slightly sinuate; not folded, flat; surface slightly bullate between the veins; glabrous and slightly glaucous both surfaces; flexible; variegated;

Leaf blade size: To about 36.8 cm long and about 24.1 cm wide about halfway from the apex; average about 33.5 cm long and 22.5 cm wide;

Leaf blade color: Early season and expanding adaxial margin nearest RHS 137A, center nearest RHS 146C with intermediate zone comprising nearest RHS 146B, abaxial margin nearest RHS N138C, center between RHS 147C and RHS 147D with intermediate zone comprising between RHS N138C and RHS 147C; mid-season and mature adaxial margin between RHS NN137B and RHS NN137C, center nearest RHS 11C with intermediate zone comprising colors of between RHS 145A and RHS N144D, between RHS N144A and RHS 145A, between RHS N144A and RHS 145B and between RHS 138A and RHS 138B, abaxial margin nearest RHS N138C, center nearest RHS 11C with intermediate zone comprising colors of between RHS 145A and RHS 144A, between RHS N144A and RHS 146D, and between RHS 145A and RHS 146D;

Veins: 12 to 13 pairs with midrib; slightly impressed adaxial and costate and smooth abaxial;

Vein color: Adaxial midrib nearest RHS NN155A, distally nearest RHS 147C and proximally nearest RHS 196B, abaxial nearest RHS 151A;

Petiole: Glabrous and matte both adaxial and abaxial; moderately concavo-convex; stiff; to 40.0 cm long and 30.0 mm wide at base and about 7.0 mm deep at base, average about 34.0 cm long and 24.0 mm wide and 6.0 mm deep;

Petiole color: Adaxial margin between RHS 145A and RHS 138A, center between RHS 145A and RHS 146D, abaxial margin nearest RHS 138A, midrib nearest RHS 145D and region surrounding midrib nearest RHS 146C; mature adaxial margin nearest RHS 137A, center nearest RHS 145D, abaxial margin nearest RHS 137A and midrib and center nearest RHS NN155B;

Flower description:

Buds one to two days prior to opening: Clavate with acute apex and narrow tube and rounded base; about 42 mm long and 12 mm in diameter at the widest portion in the bulb, tube to about 17 mm long and to about 3 mm diameter at base, tapering rapidly beyond bulb;

Bud color: Nearest RHS NN155D with a light blush nearest RHS 84D;

Flowers: Perfect; incomplete; campanulate; attitude outwardly to slightly downwardly; to 52.0 mm long to exserted pistil; corolla to 50 mm long and 30 mm wide at apex, fused in basal 31 mm, free in the distal 19.0 mm, decreasing in size distally; corolla tube portion 18 mm long and gradually tapering to 3 mm diameter at base; with rounded base; flowers tightly arranged on scape;

Flowering lasting: Persists for a normal period, usually about one day on plant;

Flowering period: Scapes remain effective with flowers beginning mid-June for about three to three and a half weeks; with about 32 flowers per scape; mostly secund;

Fragrance: No detectable fragrance;

Tepal: Two sets of three, nearly identical; clavate; entire margins; acute apex; fused in basal 31 mm; glabrous adaxial and abaxial; outer set to about 9 mm wide and 52 mm long; inner set to about 9 mm wide and 52 mm long;

Tepal color: Outer set adaxial between RHS NN155D and RHS 84D in 3 mm longitudinal center and nearest RHS NN155D along edges, abaxial between RHS NN155D and lighter than RHS 84D; inner set adaxial between RHS NN155D and RHS 84D in 3 mm longitudinal center and nearest RHS NN155D along edges, abaxial between RHS NN155D and lighter than RHS 84D, with a transparent 0.5 mm wide margin; corolla tube adaxial nearest RHS NN155C, abaxial between RHS NN155D and RHS 84D;

Gynoecium: Single; to about 52 mm long; superior;

*Style*.—Cylindrical; glabrous; to about 46 mm long and 0.7 mm diameter; straight with distal 7 mm arcuate upwards about 60°; color nearest RHS 145D proximally and RHS 155C distally.

*Stigma*.—Puberulent; globose; about 1 mm long and 1 mm diameter; color nearest RHS NN155B.

*Ovary*.—Ellipsoidal; superior; apex rounded; base rounded to truncate; sides slightly furrowed, about 5 mm long and 2.5 mm diameter; color nearest RHS 145A.

Androecium: Six;

*Filaments*.—Six; cylindrical; approximately 52 mm long and 0.5 mm in diameter; curved or bent upwardly about 90° in the distal 8 mm; color in distal one-half nearest RHS NN155A transitioning to nearest RHS 145D in the proximal one-third.

*Anthers*.—Oblong with rounded ends; basifixed, longitudinally dehiscent; about 5 mm long and 2 mm wide when fully developed; color nearest RHS 199B.

*Pollen*.—Abundant; spherical; less than 0.1mm long; color nearest RHS 12A.

Peduncle: Cylindrical; usually one per mature division; about 6 per plant; glabrous; moderately glaucous; erect to arching with maturity; to about 86 cm tall, and about 9 mm in diameter at base, average about 78 cm tall and 8 mm diameter at base;

Inflorescence: Flowering portion about 15 cm long and 7 cm wide; with single bract subtending each flower;

Peduncle color: Variable, nearest RHS N138A, nearest RHS 193B and between RHS 145C and RHS 148C;

Pedicel: Cylindrical; glabrous; slightly glaucous; to about 9 mm long and 2 mm diameter, decreasing distally; attitude outwardly in flower to arcuate downwardly with fruit;

Pedicel color: A blend between RHS 192D and RHS 84D and RHS NN155C;

Floral bracts: Each flower normally subtended by a single bract; lanceolate; narrowly acute apex and truncate base; entire margin; glabrous and slightly glaucous abaxial and adaxial; to about 22 mm long 14 mm wide, decreasing distally;

Bract color: At flowering adaxial and abaxial between RHS 76D and RHS 157C;

Fruit: Non-fleshy, dehiscent, tri-loculicidal capsule; oblong; rounded base; acute to apiculate apex; about 34 mm long and 6 mm in diameter; color as maturing nearest RHS 146D, when nearly mature and prior to dehiscence nearest RHS 150D and upon dehiscence nearest RHS 161C;

Seeds: Elliptic; with flattened wing surrounding embryo positioned toward one end of ellipse; about 7 mm long, 2.5 mm wide and 1 mm thick at embryo; typically 10 to 30 per capsule; color nearest RHS 202A with maturity;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named *Hosta* 'When I Dream' as herein described and illustrated.

* * * * *